United States Patent
Tsang et al.

(10) Patent No.: US 10,711,154 B1
(45) Date of Patent: *Jul. 14, 2020

(54) CURING AGENTS FOR HYDROPHOBIC EPOXY COMPOSITIONS

(71) Applicant: The United States of America, as represented by the Secretary of the Navy, Arlington, VA (US)

(72) Inventors: Joseph W. Tsang, Ridgecrest, CA (US); Michael Garrison, Ridgecrest, CA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 190 days.

This patent is subject to a terminal disclaimer.

(21) Appl. No.: 15/875,045

(22) Filed: Jan. 19, 2018

Related U.S. Application Data

(62) Division of application No. 14/822,346, filed on Aug. 12, 2015, now abandoned.

(51) Int. Cl.
| | |
|---|---|
| *C09D 163/00* | (2006.01) |
| *C08L 63/00* | (2006.01) |
| *C08K 3/013* | (2018.01) |
| *C07C 211/50* | (2006.01) |
| *C08K 5/00* | (2006.01) |
| *C08G 59/22* | (2006.01) |
| *C08G 59/24* | (2006.01) |
| *C08G 59/44* | (2006.01) |
| *C08G 59/50* | (2006.01) |
| *B32B 27/24* | (2006.01) |
| *B32B 27/26* | (2006.01) |
| *B32B 27/38* | (2006.01) |

(52) U.S. Cl.
CPC .......... *C09D 163/00* (2013.01); *C07C 211/50* (2013.01); *C08K 3/013* (2018.01); *C08K 5/0008* (2013.01)

(58) Field of Classification Search
None
See application file for complete search history.

(56) References Cited

U.S. PATENT DOCUMENTS

| | | | | |
|---|---|---|---|---|
| 3,427,282 A * | 2/1969 | Sundholm | .......... | C08G 59/5033 528/124 |
| 3,481,900 A * | 12/1969 | Sundholm | .......... | C08G 59/5033 528/124 |
| 3,560,443 A * | 2/1971 | Sundholm | .......... | C08G 59/5033 528/124 |
| 10,344,160 B1 * | 7/2019 | Tsang | ...................... | B32B 27/26 |

FOREIGN PATENT DOCUMENTS

| | | | | | |
|---|---|---|---|---|---|
| JP | 07238139 A | * | 9/1995 | ............. | C08G 59/24 |
| JP | 07238140 A | * | 9/1995 | ............. | C08G 59/24 |

OTHER PUBLICATIONS

Machine translation of JP-07238139-A (no date).*
Machine translation of JP-07238140-A (no date).*

* cited by examiner

*Primary Examiner* — Michael J Feely
(74) *Attorney, Agent, or Firm* — Naval Air Warfare Center Weapons Division; Stuart H. Nissim

(57) ABSTRACT

An hydrophobic epoxy resin composition including at least one ortho-substituted glycidyl ether, at least one ortho, ortho'-disubstituted glycidyl ether, at least one ortho, meta'-disubstituted glycidyl ether, at least one amine/aniline curing agent, and at least one organic solvent.

14 Claims, No Drawings

CURING AGENTS FOR HYDROPHOBIC EPOXY COMPOSITIONS

CROSS-REFERENCE TO RELATED APPLICATIONS

This is a divisional application claiming benefit of parent application Ser. No. 14/822,346 filed on Aug. 10, 2015, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to hydrophobic epoxy resin compositions including at least one ortho-alkyl substituted glycidyl ether, at least one ortho-, ortho'-dialkyl substituted glycidyl ether, at least one ortho-, meta'-dialkyl substituted glycidyl ether, at least one unsubstituted glycidyl ether, a curing agent, an optional toughener, an optical filler/pigment, and at least one organic solvent. The invention generally relates to hydrophobic anilines as curing agents for epoxy resins, and their use in combination with hydrophobic epoxy resin compositions.

DETAILED DESCRIPTION OF THE EMBODIMENTS OF THE INVENTION

Embodiments of the invention generally relate to hydrophobic epoxy resin compositions.

Structural modifications of glycidyl ether monomers described herein demonstrated significant material property improvement on epoxy resins. Since epoxies are the major resins used in fiber-reinforced composites and corrosion prevention coatings in the aerospace industry, this improvement is critical to the aircraft's safety and performance.

Water retention in composite structures induces a considerably long list of negative attributes such as: a wet-Tg knock down in use temperature, rapid heating causes catastrophic part failure, an increase in galvanic corrosion processes for neighboring/connected metal parts, and an overall weight gain for the structure. When the aircrafts operate in the humid and corrosive environments, water uptake by commercial composite resins is problematic. Water uptake by polymer matrix composite resins such as epoxies leads to a reduction of the dry-Tg or better known as wet-Tg knock down. As a consequence the resin's upper thermal operational limit is bounded by the wet-Tg, not the dry-Tg. Often the wet-Tg can be as much as 50° C. lower than the dry-Tg; therefore, this is a devastating effect on the thermo-mechanical properties of the resin and the fiber reinforced composites. Epoxies have been estimated that the Tg would decrease by 20° C. per 1% by weight of water absorbed. Herein new super-hydrophobic epoxy resins and amine-cured networks have been prepared. At the same time, processing conditions have been developed that are comparable to that of existing epoxy resin systems. When water molecules are limited to have free access to the hydrophilic and polar groups within crosslinked network, water uptake and wet-Tg knock down of cured epoxy resins have reduced significantly. Examples are shown in Invention Description section.

Alkyl substitution at the ortho-, meta- and other positions of glycidyl ethers, and at the bridging carbon between the phenolic rings have been disclosed by Niederst et al (Niederst)) for the use as protective coatings inside metal food containers. This patent described the benefits of estrogenic agonist activity of cured epoxy resins. However, there is no further teaching on the resulting material properties derived from these substituted epoxies that would relates to the present invention.

It is well established in literature that cured epoxy resins retain about 4 to 7% of water by weight (Soles). The concept of free volume and nanovoids were often described, but they are elusive quantities and difficult to measure accurately. In addition, direct correlation between free volume and water uptake is often contradicting.

From the structure perspective, several hydrophilic and polar sites within the crosslinked networks that can potentially attract and retain water through hydrogen bonding including the polyether linkages, the pendent hydroxyl- and amine groups of curing agents. This invention described the approach where hydrophobicity was systematically introduced in the epoxy backbone by substituting one or more alkyl groups at the ortho-, ortho, ortho'-, and ortho, meta'-positions of the diglycidyl ether group in the monomers. For example, a single methyl group was substituted the ortho-position (monomer A), two methyl groups at ortho, ortho'-positions (monomer B), and a large t-butyl groups at the ortho-position (monomer C) were used. Alkyl groups were also substituted at the bridging carbon between the two phenolic rings (monomer C). Examples of hydrophobic diglycidyl ethers are shown in Chemical Schematic 1.

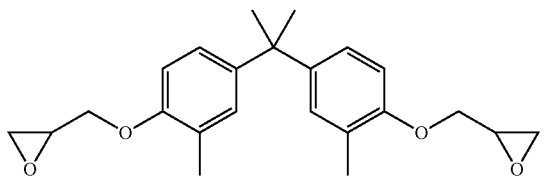 [SMILES: Cc1cc(C(C)(C)c2ccc(OCC3CO3)c(C)c2)ccc1OCC1CO1]

Diglycidyl Ether of
4,4'-Isopropylidenebis(2-methylphenol) A

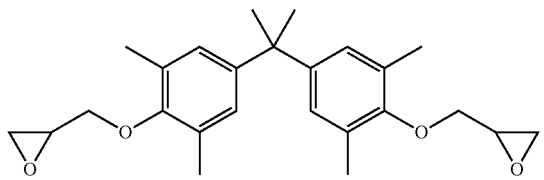 [SMILES: Cc1cc(C(C)(C)c2cc(C)c(OCC3CO3)c(C)c2)cc(C)c1OCC1CO1]

Diglycidyl Ether of
4,4-Isopropylidenebis(2,6-dimethylphenol) B

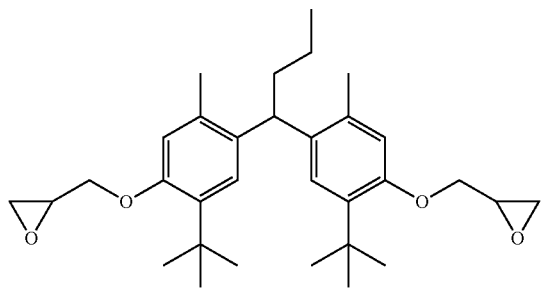 [SMILES: CCCC(c1cc(C(C)(C)C)c(OCC2CO2)cc1C)c1cc(C(C)(C)C)c(OCC2CO2)cc1C]

Diglycidyl Ether of
4,4'-Butylidenebis(2-t-butyl-5-methylphenol) C

Chemical Schematic 1. Hydrophobic glycidyl ether monomers: A, B, and C.

Monomers A, B and C were prepared from their respective bisphenols in the reaction with excess epichlorohydrin according to literature procedure (Zhou). Potassium tert-butoxide was used in place of sodium hydroxide.

These hydrophobic diglycidyl ether monomers were cured by either aliphaltic amines or anilines as curing agents. For establishing the baseline comparison, an unsubstituted diglycidyl ether of Bisphenol A, Epon 828, was used and cured with the same set of amines and aniline curing agents (Chemical Schematic 2).

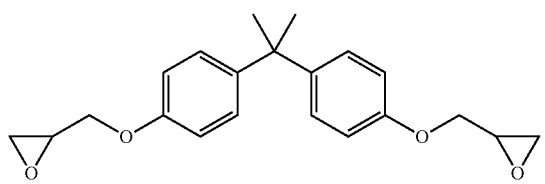 [SMILES: CC(C)(c1ccc(OCC2CO2)cc1)c1ccc(OCC2CO2)cc1]

Epon™ 828 (Diglycidyl Ether of Bisphenol A)
Chemical Schematic 2. Unsubstituted diglycidyl ether of bisphenol A (DGE BisA)

The epoxy momoner and the amine/aniline combinations were polymerized according to their stoichiometric ratios between the epoxy and amine functional groups; where phr is the parts per 100 g epoxy resin, AHEW is the amine equivalent weight, and EEW is the epoxy equivalent weight. Using the relationship, phr=AHEW*100/EEW, the epoxy equivalent weight (EEW) is used to calculate for the amount of amine/aniline curing agent with specific amine hydrogen equivalent weight (AHEW) per 100 parts resin (phr). In this invention, three aliphatic amines including hexamethylene diamine, Epikure 3175 (a polyamide), and isophorone diamine and two anilines including 4,4'-diaminodiphenyl methane and 4,4'-diaminodiphenyl sulfone were used.

The mixture was initially polymerized following the curing cycle obtained from differential scanning calorimetry (DSC). Examples 1-3 are shown for the mixing and curing.

Example 1

4,4'-Isopropylidenebis(2-methylphenol) diglycidyl ether (Monomer A), 69.1% by weight and 20% by weight of xylene were added to a vial equipped with stir bar. The solution was mixed until homogeneous. Hexamethylene diamine, 10.9% by weight (AHEW=29.1) was added and the solution was stirred at 70° C. until homogenous. The reaction mixture was put under vacuum at 70° C. for 30 minutes to degas then hot poured into aluminum containers and a silicon mold to form pucks and 20 mm×2 mm×2 mm bars, respectively. The test specimens were cured for 30 min at 70° C. (Vacuum), 4 hr at 80° C. ($N_2$), 18 hr at 150° C. ($N_2$), 24 hr at 200° C. (Vacuum).

Example 2

4,4'-Butylidenebis(2-t-butyl-5-methylphenol) diglycidyl ether (Monomer C), 66.6% by weight, and xylene, 20% by weight were added to a vial equipped with stir bar. The solution was mixed until homogeneous at 90° C. The compound 4,4'-diaminodiphenyl methane, 13.4% by weight (AHEW=49.6) was added and the solution was stirred at 90° C. until homogenous. The reaction mixture was put under vacuum at 90° C. for 30 minutes to degas then hot poured into aluminum containers and a silicon mold to form pucks and 20 mm×2 mm×2 mm bars, respectively. Test specimens were cured for 30 min at 90° C. (Vacuum), 6 hr at 100° C. ($N_2$), 18 hr at 180° C. ($N_2$), 24 hr at 265° C. (Vacuum).

Example 3

The compound 4,4'-diaminodiphenyl sulfone, 19.1% by weight (AHEW=62.1) and acetonitrile, 20% by weight were added to a vial equipped with stir bar. 4,4'-Isopropylidenebis (2,6-dimethylphenol) diglycidyl ether (Monomer B), 60.9% by weight was added and the solution was mixed at 75° C. until homogeneous. The reaction mixture was put under vacuum at 75° C. for 30 minutes to degas then was hot poured into small aluminum containers and a silicon mold to form pucks and 20 mm×2 mm×2 mm bars, respectively. The samples were heated under $N_2$ at 75° C. for 5 hr to carefully remove solvent. Test specimens were cured for 30 min at 70° C. (Vacuum), 5 hr at 75° C. ($N_2$), 18 hr at 195° C. ($N_2$), 24 hr at 250° C. (Vacuum).

For each combination of amine hardener and hydrophobic epoxy resins, the thermo-mechanical properties including dry- and wet-Tg, and % water uptake of the resulting cured resins are summarized in Tables 1-5 below. Water uptake measurements on cured resins were determined gravimetrically before and after the test pucks were heated to 100° C. in 250 ml deionized water for four days. The wet pucks were wiped dry and the wet mass was measured on an analytical balance. The weight gained as water uptake is calculated as: (Wet Mass−Dry Mass)*100%/(Dry Mass). Water uptake measurements are showed in the Tables 1-5 with the average values and their standard deviation. The dry-Tg and wet-Tg were also measured by two methods: differential scanning calorimetry (DSC) and thermos-mechanical analyzer (TMA). The difference between the dry-Tg and wet-Tg, ΔTg is Tg knock-down.

TABLE 1

Material properties of Epikcure 3175-cured epoxy networks

| | DGE BisA* | Monomer A* | Monomer B* | Monomer C* |
|---|---|---|---|---|
| Water uptake, wt % | 2.92 ± 0.09 | 2.50 ± 0.13 | 2.72 ± 0.11 | 1.45 ± 0.01 |
| Dry Tg (DSC) | 80° C. | 78° C. | 79° C. | 110° C. |
| Wet Tg (DSC) | 57° C. | 57° C. | 65° C. | 91° C. |

TABLE 1-continued

Material properties of Epikcure 3175-cured epoxy networks

|  | DGE BisA* | Monomer A* | Monomer B* | Monomer C* |
|---|---|---|---|---|
| ΔTg (DSC) | 23° C. | 21° C. | 14° C. | 19° C. |
| Dry Tg (TMA) | 74° C. | 69° C. | 69° C. | 102° C. |
| Wet Tg (TMA) | 53° C. | 54° C. | 58° C. | 93° C. |
| ΔTg (TMA) | 21° C. | 15° C. | 11° C. | 9° C. |

*DGE BisA = diglycidyl ether of bisphenol A;
Monomer A = 4,4'-Isopropylidenebis(2-methylphenol) Diglycidyl Ether;
Monomer B = 4,4'-Isopropylidenebis(2,6-dimethylphenol) Diglycidyl Ether;
Monomer C = 4,4-'-Butylidenebis(2-t-butyl-5-methylphenol) Diglycidyl Ether

TABLE 2

Material properties of hexamethylene diamine-cured epoxy networks

|  | DGE BisA* | Monomer A* | Monomer B* | Monomer C* |
|---|---|---|---|---|
| Water uptake, wt % | 3.18 ± 0.12 | 2.69 ± 0.03 | 2.83 ± 0.16 | 1.41 ± 0.04 |
| Dry Tg (DSC) | 111° C. | 106° C. | 117° C. | 118° C. |
| Wet Tg (DSC) | 84° C. | 87° C. | 94° C. | 125° C. |
| ΔTg (DSC) | 28° C. | 18° C. | 23° C. | −7° C. |
| Dry Tg (TMA) | 106° C. | 101° C. | 102° C. | 115° C. |
| Wet Tg (TMA) | 81° C. | 85° C. | 93° C. | 109° C. |
| ΔTg (TMA) | 25° C. | 17° C. | 9° C. | 7° C. |

TABLE 3

Material properties of isophorone diamine-cured epoxy networks

|  | DGE BisA* | Monomer A* | Monomer B* | Monomer C* |
|---|---|---|---|---|
| Water uptake, wt % | 2.51 ± 0.08 | 2.04 ± 0.08 | 2.17 ± 0.03 | 1.30 ± 0.04 |
| Dry Tg (DSC) | 149° C. | 125° C. | 134° C. | 162° C. |
| Wet Tg (DSC) | 114° C. | 113° C. | 115° C. | 179° C. |
| ΔTg (DSC) | 34° C. | 12° C. | 18° C. | −17° C. |
| Dry Tg (TMA) | 131° C. | 128° C. | 121° C. | 157° C. |
| Wet Tg (TMA) | 104° C. | 110° C. | 102° C. | 150° C. |
| ΔTg (TMA) | 27° C. | 18° C. | 19° C. | 7° C. |

TABLE 4

Material properties of 4,4'-diaminodiphenyl methane-cured epoxy networks

|  | DGE BisA* | Monomer A* | Monomer B* | Monomer C* |
|---|---|---|---|---|
| Water uptake, wt % | 2.70% ± 0.08 | 2.07 ± 0.04 | 1.92% ± 0.06 | 1.15% ± 0.10 |
| Dry Tg (DSC) | 173° C. | 163° C. | 169° C. | 192° C. |
| Wet Tg (DSC) | 139° C. | 147° C. | 128° C. | 181° C. |
| ΔTg (DSC) | 34° C. | 16° C. | 42° C. | 11° C. |
| Dry Tg (TMA) | 156° C. | 143° C. | 157° C. | 179° C. |
| Wet Tg (TMA) | 122° C. | 129° C. | 140° C. | 168° C. |
| ΔTg (TMA) | 34° C. | 14° C. | 17° C. | 11° C. |

TABLE 5

Material properties of 4,4'-diaminodiphenyl sulfone-cured epoxy networks

|  | DGE BisA* | Monomer A* | Monomer B* | Monomer C* |
|---|---|---|---|---|
| Water uptake, wt % | 3.86 ± 0.08 | 2.82 ± 0.11 | 2.96 ± 0.04 | Not miscible with diaminodiphenyl sulfone |

TABLE 5-continued

Material properties of 4,4'-diaminodiphenyl sulfone-cured epoxy networks

|  | DGE BisA* | Monomer A* | Monomer B* | Monomer C* |
|---|---|---|---|---|
| Dry Tg (DSC) | 218° C. | 163.7° C. | 195° C. |  |
| Wet Tg (DSC) | 185° C. | 125.7° C. | 195° C. |  |
| ΔTg (DSC) | 33° C. | 38.0° C. | 0.4° C. |  |
| Dry Tg (TMA) | 205° C. | 158.6° C. | 187° C. |  |
| Wet Tg (TMA) | 149° C. | 115.5° C. | 141° C. |  |
| ΔTg (TMA) | 56° C. | 43.1° C. | 45° C. |  |

Results on water uptake and wet Tg knock-down showed substantial improvement in all epoxy-amine/aniline combinations as shown in Tables 1-5. The level of improvement is unanticipated on the basis of free volume consideration in these new networks. As shown in Table 6 below, the substituted epoxies, monomer A, monomer B, and monomer C, have the lower density values comparing to the corresponding amine-cured unsubstituted epoxies. This indicated that higher free volumes exist in these substituted-epoxy networks should absorbing more water and having large wet Tg knock-down. However, the data in Table 6 do not support this. In fact, the opposite effect is found in the testing. Curing agents with hydrophobic monomers A, B and C have the lower % water uptake and wet Tg knock-down values. The only compound, 4,4'-diaminodiphenyl sulfone in this invention, was the only curing agent that is difficult to fully polymerize due to poor solubility, as in the case of the most hydrophobic monomer C. Monomers A and B polymerized well with 4,4% diaminodiphenyl sulfone.

TABLE 6

Density Measurement of epoxy-amine/aniline cured resins

| Resin | Curing Agent | Solvent | Density (g/mL) Run 1 | Density (g/mL) Run 2 |
|---|---|---|---|---|
| DGE BisA | Epikure 3175 | p-Xylenes | 1.1343 ± 0.0031 | 1.1291 ± 0.0027 |
| Monomer A | Epikure 3175 | p-Xylenes | 1.1117 ± 0.0017 | 1.1126 ± 0.0014 |
| Monomer B | Epikure 3175 | p-Xylenes | 1.0941 ± 0.0023 | 1.0951 ± 0.0018 |
| Monomer C | Epikure 3175 | p-Xylenes | 1.0330 ± 0.0008 | 1.0426 ± 0.0020 |
| DGE BisA | Hexamethylene Diamine | Acetonitrile | 1.1524 ± 0.0039 | 1.1542 ± 0.0034 |
| DGE BisA | Hexamethylene Diamine | p-Xylenes | 1.1559 ± 0.0022 | 1.1598 ± 0.0026 |
| Monomer A | Hexamethylene Diamine | p-Xylenes | 1.1088 ± 0.0010 | 1.1301 ± 0.0007 |
| Monomer B | Hexamethylene Diamine | p-Xylenes | 1.0784 ± 0.0013 | 1.0592 ± 0.0018 |
| Monomer C | Hexamethylene Diamine | p-Xylenes | 1.0265 ± 0.0005 | 1.0268 ± 0.0003 |
| DGE BisA | Isophorone Diamine | Acetonitrile | 1.1369 ± 0.0022 | 1.1356 ± 0.0031 |
| DGE BisA | Isophorone Diamine | p-Xylenes | 1.1353 ± 0.0007 | 1.1371 ± 0.0032 |
| Monomer A | Isophorone Diamine | p-Xylenes | 1.1121 ± 0.0011 | 1.1165 ± 0.0021 |
| Monomer B | Isophorone Diamine | p-Xylenes | 1.0871 ± 0.0012 | 1.0809 ± 0.0020 |
| Monomer C | Isophorone Diamine | p-Xylenes | 1.0144 ± 0.0019 | 1.0141 ± 0.0017 |
| DGE BisA | 4,4'-diaminodiphenyl methane | p-Xylenes | 1.1902 ± 0.0012 | 1.1884 ± 0.0018 |
| Monomer A | 4,4'-diaminodiphenyl methane | p-Xylenes | 1.1656 ± 0.0007 | 1.1625 ± 0.0030 |

TABLE 6-continued

Density Measurement of epoxy-amine/aniline cured resins

| Resin | Curing Agent | Solvent | Density (g/mL) Run 1 | Density (g/mL) Run 2 |
|---|---|---|---|---|
| Monomer B | 4,4'-diaminodiphenyl methane | p-Xylenes | 1.1327 ± 0.0014 | 1.1323 ± 0.0029 |
| Monomer C | 4,4'-diaminodiphenyl methane | p-Xylenes | 1.0542 ± 0.0007 | 1.0535 ± 0.0014 |
| DGE BisA | 4,4'-diaminodiphenyl sulfone | Acetonitrile | 1.2175 ± 0.0025 | 1.2178 ± 0.0069 |
| Monomer A | 4,4'-diaminodiphenyl sulfone | Acetonitrile | 1.2013 ± 0.0009 | 1.2015 ± 0.0029 |
| Monomer B | 4,4'-diaminodiphenyl sulfone | Acetonitrile | 1.1680 ± 0.0005 | 1.1704 ± 0.0013 |

Another new teaching in this invention is related to the formation of hydrogen bonding formation between water molecules and multiple polar groups within the networks such as the polyether linkages, the pendent hydroxyl- and amine groups of curing agents. When alkyl groups are systematically introduced in the diglycidyl ethers, they effectively shielded the polar groups from forming the multiple hydrogen bonds to water molecules. Results in Tables 1-5 showed that a progressive decrease in % water uptake going from an unsubstituted epoxy (as the baseline resin) to a single methyl group in ortho-substitution, two methyl groups in ortho, ortho'-disubstitution, and a large tert-butyl group and a methyl group in ortho, meta'-substitution. This hydrophobicity and water uptake relationship is consistent throughout this invention as shown in Tables 1-5.

In another aspect of new teaching in this invention, water uptake measurement of epoxy-amine/aniline combinations are normalized based on the molecular weight, available lone pair electrons, and polar groups, and expressed as normalized water uptake in milli-mole of $H_2O$ per mole of hydrogen bonding site (HBS). The normalized results as shown in Table 7 provide a complete accounting on the accessibility to hydrogen bonding sites within the cured resins that correlate directly to water uptake and hydrophobicity. For example, there are two lone pairs of electrons on each ether group, —O— and the glycidyl ether groups. Thus, there are eight pairs of lone electrons for each diglycidyl ether monomer. For each amine/aniline, there is one lone pair electron on the nitrogen and two active hydrogens, After the reaction with a glycidyl ether group that hydrogen would form the hydroxyl group, thus the number of polar groups remain constant. The compound, 4,4'-diaminodiphenyl sulfone has additional four lone pair electrons on the bridging sulfone, —$SO_2$— groups.

TABLE 7

Normalized Water Uptake Measurements

| Resin | Curing Agent | Solvent | Normalized Water Uptake (mmol $H_2O$/mol HBS) |
|---|---|---|---|
| DGE BisA | Hexamethylene Diamine | Acetonitrile | 64.5 ± 2.4 |
| DGE BisA | Hexamethylene Diamine | p-Xylenes | 65.1 ± 3.5 |
| Monomer A | Hexamethylene Diamine | p-Xylenes | 79.0 ± 2.1 |
| Monomer B | Hexamethylene Diamine | p-Xylenes | 65.0 ± 3.6 |
| Monomer C | Hexamethylene Diamine | p-Xylenes | 32.3 ± 1.0 |
| DGE BisA | Isophorone Diamine | Acetonitrile | 54.0 ± 1.8 |
| DGE BisA | Isophorone Diamine | p-Xylenes | 54.6 ± 3.8 |
| Monomer A | Isophorone Diamine | p-Xylenes | 61.2 ± 0.4 |
| Monomer B | Isophorone Diamine | p-Xylenes | 52.8 ± 0.6 |
| Monomer C | Isophorone Diamine | p-Xylenes | 37.9 ± 1.2 |
| DGE BisA | 4,4'-diaminodiphenyl methane | p-Xylenes | 60.0 ± 1.9 |
| Monomer A | 4,4'-diaminodiphenyl methane | p-Xylenes | 44.4 ± 1.2 |
| Monomer B | 4,4'-diaminodiphenyl methane | p-Xylenes | 47.9 ± 1.5 |
| Monomer C | 4,4'-diaminodiphenyl methane | p-Xylenes | 34.3 ± 2.8 |
| DGE BisA | 4,4'-diaminodiphenyl sulfone | Acetonitrile | 77.3 ± 1.7 |
| Monomer B | 4,4'-diaminodiphenyl sulfone | Acetonitrile | 72.7 ± 1.1 |

Results in Table 7 reaffirmed that a decrease in normalized water uptake corresponds to the increased in hydrophobicity on each series of alkyl-substituted epoxy-amine/aniline combination. Most notably, the large tert-butyl group in the ortho-position has the largest magnitude of water uptake decreases. These results support that hydrogen bonding to multiple polar groups is necessary to retain water. Large hydrophobic alkyl groups strategically substituted on the phenolic ring will limit water molecules to gain access to sites where both the ether and adjacent hydroxyl group are situated. Although the alkyl-substitution approach is not obvious and yet the hydrophobic effect imposed on water uptake in cured networks is significant.

In another aspect of this invention is that these hydrophobic epoxy resin compositions can be formulated as two-part systems for coatings application, while one-part systems can be formulated to prepare fiber-reinforced prepeg in the manufacturing of fiber-reinforced composite laminates and structures.

It is well known to those skillful in the arts of formulating reactive epoxy systems for coating applications using aliphatic amines as curing agents. In two-part systems, Part A (resins) and B (curing agents) are formulated and kept separately to prevent premature polymerization. Once they are mixed according to their stoichiometric ratios between the epoxy and amine/aniline functional groups, there is a finite pot-life at which gelation occurs that would prevent the formation of uniform coatings. Therefore, the epoxy mixtures must be applied before the gel point. Part A is formulated to have at least one ortho-alkyl substituted glycidyl ether, at least one ortho-, ortho'-dialkyl substituted glycidyl ether; at least one ortho-, meta'-dialkyl substituted glycidyl ether, at least one unsubstituted glycidyl ether or any combinations thereof, one organic solvent. Part B is formulated to have at least one curing agent and at least one organic solvent.

It is also well known to those skillful in the arts of formulating one-part system using latent curing agents such as anilines. An one-part system can be formulated to have at least one ortho-alkyl substituted glycidyl ether, at least one ortho-, ortho'-dialkyl substituted glycidyl ether; at least one ortho-, meta'-dialkyl substituted glycidyl ether, at least one unsubstituted glycidyl ether or any combinations thereof, at least one curing agent and at least one organic solvent. One-part epoxy systems can be used in the preparation of prepeg. Commonly used fiber-reinforced materials are woven and non-woven clothes and honeycomb structures made from carbon fiber, glass fiber, aramid, silicon nitride, silicon carbide and other ceramic compounds. Multiple layers of prepeg are stacked, heated while under pressure laminated structures.

An aspect of the invention generally relates to hydrophobic epoxy resin compositions including at least one ortho-alkyl substituted glycidyl ether, at least one ortho, ortho'-dialkyl substituted glycidyl ether, at least one ortho, meta'-dialkyl substituted glycidyl ether, at least one unsubstituted glycidyl ether and the combination thereof, at least one curing agent, and at least one organic solvent. Embodiments further include at least one toughener and/or at least one filler/pigment. In embodiments, the ortho-alkyl substituted glycidyl ethers include at least two epoxy functional groups, where $R_1$, $R_2$, and $R_3$ are $C_1$-$C_{10}$;

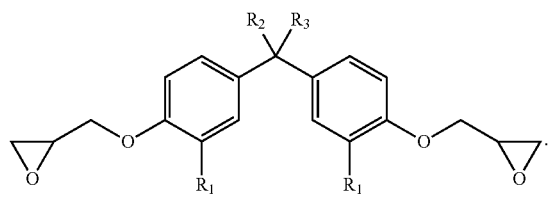

In embodiments, the ortho, ortho'-dialkyl substituted glycidyl ether include at least two epoxy functional groups, where $R_1$, $R_2$, $R_3$, and $R_4$ are $C_1$-$C_{10}$;

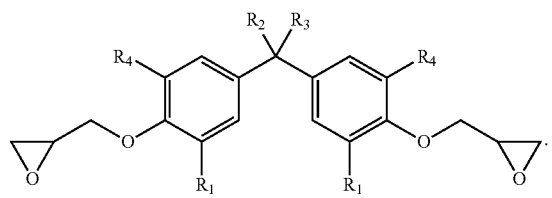

In embodiments, the ortho, meta'-dialkyl substituted glycidyl ethers are comprised of at least two epoxy functional groups, where $R_1$, $R_2$, $R_3$, and $R_4$ are $C_1$-$C_{20}$;

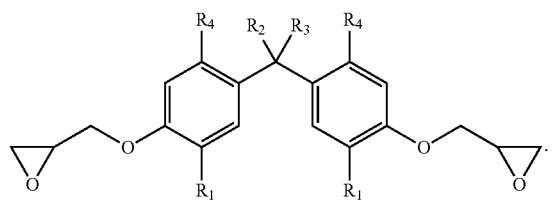

In embodiments, the glycidyl ethers include at least two epoxy functional groups with a molecular weight in the range of 300 to 2,000 and an epoxy equivalent weight in the range of 100-400. In embodiments, the curing agents for said glycidyl ethers are selected from the group consisting of at least one polyanilines, aliphatic polyamines, and polyamides with amine hydrogen equivalent weight in the range of about 20-400. In embodiments, the polyanilines having at least two primary and secondary amine functional groups or combinations thereof, and are in the range of about $C_6$-$C_{18}$. In embodiments, the aliphatic polyamines having at least two primary, secondary, and tertiary amine functional groups or combinations thereof, and are in the range of about $C_4$-$C_{30}$. In embodiments, the polyamides having at least two primary and secondary amine functional groups or combinations thereof, and are in the range of about $C_4$-$C_{30}$. In embodiments, the tougheners for cured epoxies are selected from the group consisting of thermoplastics, elastomers, reactive elastomers in the range of 1% by weight to about 20% by weight. In embodiments, the fillers or pigments are selected from the group consisting of inorganic and organic compounds in the range of 1% by weight to about 20% by weight.

In embodiments, the organic solvents are selected from the group consisting of aromatic hydrocarbons of about $C_6$-$C_{10}$, ketones, phenols, amides, nitriles, and glycols, or in any combinations thereof. In other embodiments, the organic solvents are in the range of about 0.5% by weight to 0.50% by weight. In embodiments, the boiling points of the organic solvents are in the range of about 40-200° C.

Another aspect of the invention relates to a system for making hydrophobic epoxy resin having a two-part system including, a first part is formulated of at least one ortho-alkyl substituted glycidyl ether, at least one ortho, ortho'-dialkyl substituted glycidyl ether; at least one ortho, meta'-dialkyl substituted glycidyl ether, at least one unsubstituted glycidyl ether or any combinations thereof, one organic solvent; and a second part is formulated of at least one curing agent and at least one organic solvent, where the first part and the second part are combined and polymerized to produce hydrophobic epoxy resin compositions. Embodiments further include at least one toughener and/or at least one filler/pigment of the second part.

In embodiments, the first part and the second part are stored separately before combining to produce the hydrophobic epoxy resin composition. Embodiments further include mixing the first and second parts forming an epoxy mixture coating where the epoxy equivalent weight (resin) and the amine hydrogen equivalent weight (curing agent), applying the coating onto a substrate and curing to form a crosslinked network. In embodiments, the epoxy mixture is applied by low pressure spraying, rolling, brushing and mold transferring methods.

Another aspect of the invention generally relates to another system for making hydrophobic epoxy resin compositions including a one part system having one part resin being formulated of at least one ortho-alkyl substituted glycidyl ether, at least one ortho, ortho'-dialkyl substituted glycidyl ether; at least one ortho, meta'-dialkyl substituted glycidyl ether, at least one unsubstituted glycidyl ether or any combinations thereof, at least one amine/aniline curing agent, at least one organic solvent, where the mixture heated and polymerize to produce epoxy resin compositions. Yet another aspect of the invention generally relates to methods to form fiber-reinforced polymer matrix composites, including, a one-part resin being formulated of at least one ortho-alkyl substituted glycidyl ether, at least one ortho, ortho'-dialkyl substituted glycidyl ether; at least one ortho-, meta'-dialkyl substituted glycidyl ether, at least one unsubstituted glycidyl ether or any combinations thereof, at least one curing agent and at least one organic solvent, where the mixture forms hydrophobic epoxy resin compositions, where the epoxy resin composition is used to impregnate woven or non-woven fiber cloth, and where at least two plies of resin impregnated cloth and cure under temperature and pressure to form composite laminates. In embodiments, the curing of the composite laminates are accomplished by selecting on of the group consisting of out-of-autoclave, vacuum assisted resin transfer molding, film infusion, and autoclave methods.

Another aspect of the invention teaches a new approach to improve the material properties of epoxy resins while maintains existing fiber prepreg preparation and the curing processes of fiber reinforced composites. Significant improvements in reducing moisture uptake reduction and wet-Tg knockdown have been showed by curing with hydrophobic anilines. Since epoxies are the major resins used in fiber-reinforced composites and corrosion prevention coatings in the aerospace industry, this improvement is critical to the aircraft's safety and performance.

Water retention in composite structures induces a considerably long list of negative attributes such as: a wet-Tg knock down in use temperature, rapid heating causes catastrophic part failure, an increase in galvanic corrosion processes for neighboring/connected metal parts, and an overall weight gain for the structure. When the aircrafts operate in the humid and corrosive environments, water uptake by commercial composite resins is problematic. Water uptake by polymer matrix composite resins such as epoxies leads to a reduction of the dry-Tg or better known as wet-Tg knock down. As a consequence the resin's upper thermal operational limit is bounded by the wet-Tg, not the dry-Tg. Often the wet-Tg can be as much as 50° C. lower than the dry-Tg; therefore, this is a devastating effect on the thermo-mechanical properties of the resin and the fiber reinforced composites. Epoxies have been estimated that the Tg would decrease by 20° C. per 1% by weight of water absorbed (Wright). Herein new super-hydrophobic epoxy resins and amine-cured networks have been prepared. At the same time, processing conditions have been developed that are comparable to that of existing epoxy resin systems. When water molecules are limited to have free access to the hydrophilic and polar groups within crosslinked network, water uptake and wet-Tg knock down of cured epoxy resins have reduced significantly. Examples are shown in Invention Description section.

Alkyl substitution at the ortho-, meta- and other positions on glycidyl ethers, and at the bridging carbon between the phenolic rings have been disclosed by Niederst et al for the use as protective coatings inside metal food containers. This patent described the benefits of estrogenic agonist activity of cured epoxy resins. However, there is no further teaching on the resulting material properties derived from these substituted epoxies that would relates to the present invention.

It is well established in the literature that cured epoxy resins retain about 4 to 7% of water by weight (Soles). Several polar and hydrophilic sites within the crosslinked resins can potentially attract and retain water including the polyether linkages, the pendent hydroxyl- and amine groups. Hydrophobicity was systematically introduced in the crosslinked networks by incorporating one or more ortho-substituted alkyl groups on the anilines as the amine-hardeners to cure epoxy resins (see Chemical Schematics 2a-2c). Although small alkyl groups such as methyl and ethyl groups, are used in this invention, but they should not impede on the scope of the invention. Larger alkyl groups are anticipated as long as they are not overly sterically hindered on the amine functional group in the ortho-position and slow down the addition reaction to glycidyl ether groups. The chemical structures are shown below.

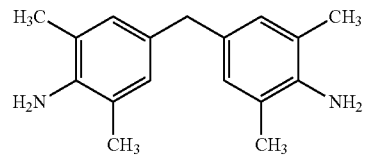

Chemical Schematic 2 (a)

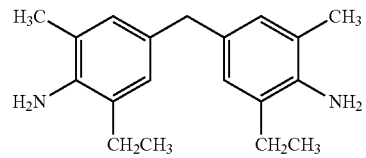

Chemical Schematic 2 (b)

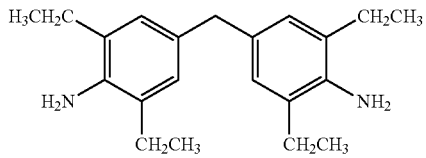

Chemical Schematic 2 (c)

Chemical Schematic 2 (a-c). Hydrophobic di-aniline curing agents: (a) 4,4'-diamino-3,3'-dimethyldiphenyl methane, (b) 4,4'-isopropylidenebis(2,6-dimethylphenol) and (c) 4,4'-Methylenebis(2,6-diethylaniline)

When these alkyl-substituted anilines were to cure with epoxy resins including the alkyl substituted epoxy resins, water uptakes were reduced substantially than the unsubstituted dianilines as shown in Tables 1-4. The increase of hydrophobicity on the anilines substantially decreases the water uptake and wet-Tg knock-down on fully cured epoxy resins. This is a result of a more hydrophobic environment is being created around the polar and hydrophilic sites and limiting water molecules freely diffuse into the crosslinked network. Results on curing agents, dry- and wet glass transition temperatures (Tg), water uptakes are listed on Tables 1-4.

TABLE 1

Material properties of diaminophenyl methane-cured epoxy resins

|  | DGE BisA* | Monomer A* | Monomer B* | Monomer C* |
| --- | --- | --- | --- | --- |
| Water uptake, wt % | 2.70 ± 0.08 | 2.07 ± 0.04 | 1.92 ± 0.06 | 1.15 ± 0.10 |
| Dry Tg (DSC) | 173° C. | 163° C. | 169° C. | 192° C. |
| Wet Tg (DSC) | 139° C. | 147° C. | 128° C. | 181° C. |
| ΔTg (DSC) | 34° C. | 16° C. | 42° C. | 11° C. |
| Dry Tg (TMA) | 156° C. | 143° C. | 157° C. | 179° C. |
| Wet Tg (TMA) | 122° C. | 129° C. | 140° C. | 168° C. |
| ΔTg (TMA) | 34° C. | 14° C. | 17° C. | 11° C. |

*DGE BisA = diglycidyl ether of bisphenol A;
Monomer A = 4,4'-Isopropylidenebis(2-methylphenol) Diglycidyl Ether;
Monomer B = 4,4'-Isopropylidenebis(2,6-dimethylphenol) Diglycidyl Ether;
Monomer C = 4,4'-Butylidenebis(2-t-butyl-5-methylphenol) Diglycidyl Ether Results in Tables 1-4 showed that the water uptake and wet Tg knock-down have substantially improved in all epoxy-aniline combinations. The most hydrophobic combination of 4,4'-methylenebis(2,6-diethylaniline) and 4,4'-butylidenebis(2-t-butyl-5-methylphenol) diglycidyl ether provided water uptake at 0.87% by weight, the lowest value reported in literature for aniline-cured epoxies. As a result, both the dry and wet Tg are higher than those of the corresponding un-substituted aniline-epoxy combination. The wet Tg knock-down is only 4° C. lower than the dry Tg. The level of improvement is unanticipated on the basis of free volume consideration in these new networks. Density measurement shown in Table 5 indicated that more substituted anilines have the lower density in the network. This indicated that higher free volumes exist in these aniline-epoxy networks should absorbing more water and having large wet Tg knock-down. However, the data in Table 5 do not support this. In fact, the opposite effect is found in the testing.

TABLE 2

Material properties of 4,4'-diamino-3,3'-dimethyldiphenyl methane-cured epoxy resins

|  | DGE BisA* | Monomer A* | Monomer B* | Monomer C* |
|---|---|---|---|---|
| Water uptake, wt % | 2.42 ± 0.08 | 1.99 ± 0.03 | 2.49 ± 0.50 | 1.09 ± 0.01 |
| Dry Tg (DSC) | 140° C. | 127° C. | 140° C. | 138° C. |
| Wet Tg (DSC) | 124° C. | 115° C. | 115° C. | 137° C. |
| ΔTg (DSC) | 16° C. | 12° C. | 25° C. | 1° C. |
| Dry Tg (TMA) | 104° C. | 119° C. | 130° C. | 132° C. |
| Wet Tg (TMA) | 87° C. | 104° C. | 109° C. | 126° C. |
| ΔTg (TMA) | 17° C. | 15° C. | 21° C. | 6° C. |

TABLE 3

Material properties of 4,4'-Methylenebis(2-ethyl-6-methylaniline)-cured epoxy resins

|  | DGE BisA* | Monomer A* | Monomer B* | Monomer C* |
|---|---|---|---|---|
| Water uptake, wt % | 1.95 ± 0.05 | 1.43 ± 0.04 | 1.51 ± 0.07 | 0.93 ± 0.03 |
| Dry Tg (DSC) | 179° C. | 145° C. | 134° C. | 173° C. |
| Wet Tg (DSC) | 161° C. | 130° C. | 119° C. | 173° C. |
| ΔTg (DSC) | 18° C. | 15° C. | 16° C. | 0.3° C. |
| Dry Tg (TMA) | 165° C. | 140° C. | 132° C. | 162° C. |
| Wet Tg (TMA) | 146° C. | 121° C. | 108° C. | 159° C. |
| ΔTg (TMA) | 19° C. | 18° C. | 24° C. | 3° C. |

TABLE 4

Material properties of 4,4'-Methylenebis(2,6-diethylaniline)-cured epoxy resins

|  | DGE BisA* | Monomer A* | Monomer B* | Monomer C* |
|---|---|---|---|---|
| Water uptake, wt % | 1.95 ± 0.06 | 1.34 ± 0.01 | 1.47 ± 0.02 | 0.87 ± 0.04 |
| Dry Tg (DSC) | 156° C. | 141° C. | 133° C. | 170° C. |
| Wet Tg (DSC) | 126° C. | 123° C. | 121° C. | 159° C. |
| ΔTg (DSC) | 30° C. | 17° C. | 13° C. | 11° C. |
| Dry Tg (TMA) | 144° C. | 130° C. | 122° C. | 158° C. |
| Wet Tg (TMA) | 129° C. | 118° C. | 112° C. | 154° C. |
| ΔTg (TMA) | 15° C. | 12° C. | 10° C. | 4° C. |

TABLE 5

Density Measurement of substituted aniline-cured epoxy resins

| Resin | Curing Agent | Solvent | Density (g/mL) Run 1 | Density (g/mL) Run 2 |
|---|---|---|---|---|
| DGE BisA | 4,4'-diaminodiphenyl methane | p-Xylenes | 1.1902 ± 0.0012 | 1.1884 ± 0.0018 |
| Monomer A | 4,4'-diaminodiphenyl methane | p-Xylenes | 1.1656 ± 0.0007 | 1.1625 ± 0.0030 |
| Monomer B | 4,4'-diaminodiphenyl methane | p-Xylenes | 1.1327 ± 0.0014 | 1.1323 ± 0.0029 |
| Monomer C | 4,4'-diaminodiphenyl methane | p-Xylenes | 1.0542 ± 0.0007 | 1.0535 ± 0.0014 |
| DGE BisA | 4,4'-diamino-3,3'-dimethyldiphenyl methane | p-Xylenes | 1.1747 ± 0.0036 | 1.1738 ± 0.0002 |
| Monomer A | 4,4'-diamino-3,3'-dimethyldiphenyl methane | p-Xylenes | 1.1310 ± 0.0015 | 1.1221 ± 0.0013 |
| Monomer B | 4,4'-diamino-3,3'-dimethyldiphenyl methane | p-Xylenes | 1.1145 ± 0.0059 | 1.1143 ± 0.0022 |
| Monomer C | 4,4'-diamino-3,3'-dimethyldiphenyl methane | p-Xylenes | 1.0522 ± 0.0030 | 1.0514 ± 0.0023 |
| DGE BisA | 4,4'-Methylenebis(2-ethyl-6-methylaniline) | p-Xylenes | 1.1461 ± 0.0006 | 1.1470 ± 0.0016 |
| Monomer A | 4,4'-Methylenebis(2-ethyl-6-methylaniline) | p-Xylenes | 1.1302 ± 0.0006 | 1.1283 ± 0.0010 |
| Monomer B | 4,4'-Methylenebis(2-ethyl-6-methylaniline) | p-Xylenes | 1.1101 ± 0.0014 | 1.1115 ± 0.0010 |
| Monomer C | 4,4'-Methylenebis(2-ethyl-6-methylaniline) | p-Xylenes | 1.0505 ± 0.0013 | 1.0553 ± 0.0065 |
| DGE BisA | 4,4'-Methylenebis(2,6-diethylaniline) | p-Xylenes | 1.1354 ± 0.0021 | 1.1381 ± 0.0016 |
| Monomer A | 4,4'-Methylenebis(2,6-diethylaniline) | p-Xylenes | 1.1194 ± 0.0012 | 1.1258 ± 0.0019 |
| Monomer B | 4,4'-Methylenebis(2,6-diethylaniline) | p-Xylenes | 1.0984 ± 0.0038 | 1.0980 ± 0.0031 |
| Monomer C | 4,4'-Methylenebis(2,6-diethylaniline) | p-Xylenes | 1.0282 ± 0.0014 | 1.0282 ± 0.0032 |

*DGE BisA = diglycidyl ether Bisphenol A;
MonomerA = 4,4'-isopropylidenebis(2-methylphenol);
Monomer B = 4,4'-isopropylidenebis(2,6-dimethylphenol);
Monomer C = 4,4'-butylidenebis(2-t-butyl-5-methylphenol Another new teaching in this invention is related to the significance of hydrogen bonding formation between water molecules and multiple polar groups within the networks. Examples of polar groups are the polyether linkages, the pendent hydroxyl- and amine groups of curing agents. When an alkyl group is substituted at the ortho position to the amino group, water molecules are less accessible to the nitrogen's lone pair electrons through hydrogen bonding and a reduced water uptake is thus observed. Water uptake is reduced further when the alkyl group increased from a methyl to an ethyl group. Most likely it is due to fact that nitrogen's lone pair electrons are good acceptor to the hydrogen of water molecules as the donor. When the hydrophobic anilines are cured with hydrophobic glycidyl ethers, the size and location of alkyl substitution of both compounds strongly affect the access to potential water bonding sites and the consequence of water uptake. These results support that multiple hydrogen bonding are formed with water molecules on several potential polar groups within the network.

In another aspect of new teaching in this invention, water uptake measurement of epoxy-aniline combinations are normalized based on the molecular weight, available lone pair electrons, and polar groups, and expressed as normalized water uptake in milli-mole of $H_2O$ per mole of hydrogen bonding site (HBS). The normalized results as shown in Table 6 provide a complete accounting on the accessibility to hydrogen bonding sites within the cured resins that correlate directly to water uptake and hydrophobicity. For example, there are two lone pairs of electrons on each ether group, —O— and the glycidyl ether groups. Thus, there are eight pairs of lone electrons for each diglycidyl ether monomer. For each amine/aniline, there is one lone pair electron on the nitrogen and two active hydrogens. After the reaction with a glycidyl ether group that hydrogen would form the hydroxyl group, thus the number of polar groups remain constant. The compound, 4,4'-diaminodiphenyl sulfone has additional four lone pair electrons on the bridging sulfone, —$SO_2$— groups.

TABLE 6

Normalized Water Uptake Measurements

| Resin | Curing Agent | Solvent | Normalized Moisture Uptake (mmol $H_2O$/ mol HBS) |
| --- | --- | --- | --- |
| DGE BisA | 4,4'-diaminodiphenyl methane | p-Xylenes | 60.0 ± 1.9 |
| Monomer A | 4,4'-diaminodiphenyl methane | p-Xylenes | 44.4 ± 1.2 |
| Monomer B | 4,4'-diaminodiphenyl methane | p-Xylenes | 47.9 ± 1.5 |
| Monomer C | 4,4'-diaminodiphenyl methane | p-Xylenes | 34.3 ± 2.8 |
| DGE BisA | 4,4'-diamino-3,3'-dimethyldiphenyl methane | p-Xylenes | 55.3 ± 1.7 |
| Monomer A | 4,4'-diamino-3,3'-dimethyldiphenyl methane | p-Xylenes | 48.5 ± 0.7 |
| Monomer B | 4,4'-diamino-3,3'-dimethyldiphenyl methane | p-Xylenes | 64.1 ± 12.9 |
| Monomer C | 4,4'-diamino-3,3'-dimethyldiphenyl methane | p-Xylenes | 33.4 ± 0.3 |
| DGE BisA | 4,4'-Methylenebis (2-ethyl-6-methylaniline) | p-Xylenes | 47.2 ± 1.1 |
| Monomer A | 4,4'-Methylenebis (2-ethyl-6-methylaniline) | p-Xylenes | 36.8 ± 1.0 |
| Monomer B | 4,4'-Methylenebis (2-ethyl-6-methylaniline) | p-Xylenes | 40.8 ± 1.9 |
| Monomer C | 4,4'-Methylenebis (2-ethyl-6-methylaniline) | p-Xylenes | 29.9 ± 1.2 |

TABLE 6-continued

Normalized Water Uptake Measurements

| Resin | Curing Agent | Solvent | Normalized Moisture Uptake (mmol $H_2O$/ mol HBS) |
| --- | --- | --- | --- |
| DGE BisA | 4,4'-Methylenebis(2,6-diethylaniline) | p-Xylenes | 48.6 ± 1.5 |
| Monomer A | 4,4'-Methylenebis(2,6-diethylaniline) | p-Xylenes | 35.3 ± 0.2 |
| Monomer B | 4,4'-Methylenebis(2,6-diethylaniline) | p-Xylenes | 41.2 ± 0.6 |
| Monomer C | 4,4'-Methylenebis(2,6-diethylaniline) | No Solvent | 28.5 ± 1.3 |
| Monomer C | 4,4'-Methylenebis(2,6-diethylaniline) | p-Xylenes | 29.0 ± 0.5 |

An aspect of the invention generally relates to curing agents for preparing hydrophobic epoxy compositions including, at least one ortho-substituted dianilines, at least one ortho, ortho'-substituted dianilines, and where dianilines having $R_1$ and $R_2$ are $C_1$-$C_{10}$, and X is alkyl, branched alkyl, CO, O, S, and $SO_2$,

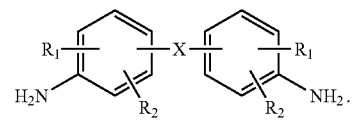

In embodiments, the alkyl $R_1$ and $R_2$ groups having a hydrodynamic radius equal to or greater than that of aromatic carbon bonded to the nitrogen atom. Another aspect of the invention generally relates to hydrophobic epoxy resin compositions including, at least one ortho-substituted glycidyl ether, at least one ortho, ortho'-disubstituted glycidyl ether, at least one ortho, meta'-disubstituted glycidyl ether, at least one curing agent including at least one ortho-substituted dianilines and/or at least one ortho, ortho'-substituted dianilines, where the dianilines having $R_1$ and $R_2$ are $C_1$-$C_{10}$, and X is alkyl, branched alkyl, CO, O, S, and $SO_2$,

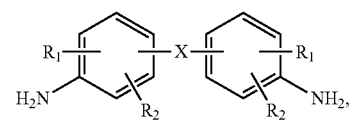

and at least one organic solvent.

Embodiments further include at least one toughener and/or at least one filler/pigment. In embodiments, the ortho-alkyl substituted glycidyl ethers include at least two epoxy functional groups, where the $R_1$, $R_2$, and $R_3$ are $C_1$-$C_{10}$,

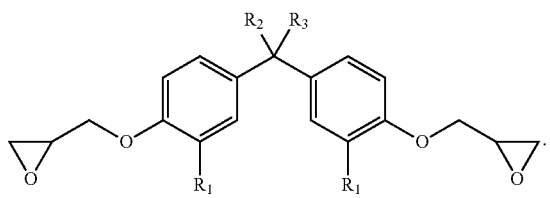

In embodiments, the ortho, ortho'-dialkyl substituted glycidyl ether include at least two epoxy functional groups, where the $R_1$, $R_2$, $R_3$, and $R_4$ are $C_1$-$C_{10}$,

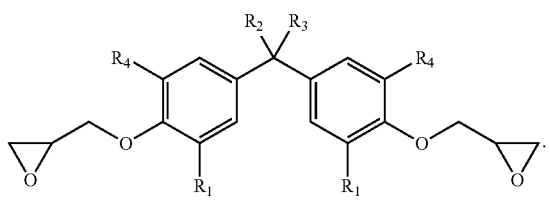

In embodiments, the ortho, meta-dialkyl substituted glycidyl ethers are comprised of at least two epoxy functional groups, wherein said $R_1$, $R_2$, $R_3$, and $R_4$ are $C_1$-$C_{20}$,

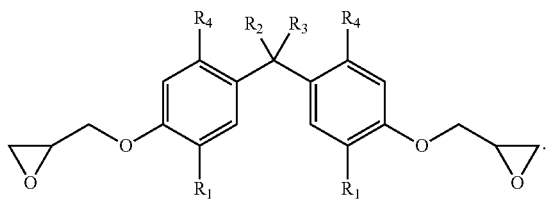

In embodiments, the glycidyl ethers include at least two epoxy functional groups with a molecular weight of 1,000 to 6,000 and an epoxy equivalent weight in the range of 100-300.

Embodiments further include additional curing agents for the glycidyl ethers and are selected from the group consisting of at least one polyanilines, aliphatic polyamines, and polyamides with amine hydrogen equivalent weight in the range of about 20-200. In embodiments, the tougheners are for cured epoxies and are selected from the group consisting of thermoplastics, elastomers, reactive elastomers in the range of 1% by weight to about 20% by weight. In embodiments, the fillers or pigments are selected from the group consisting of inorganic and organic compounds in the range of 1% by weight to about 20% by weight. In embodiments, the organic solvents are selected from the group consisting of aromatic hydrocarbons of about $C_6$-$C_{10}$, ketones, phenols, amides, nitriles, and glycols, or in any combinations thereof. In other embodiments, the organic solvents are in the range of about 0.5% by weight to 50% by weight. In embodiments, the boiling points of the organic solvents are in the range of about 40-200° C.

Another aspect of the invention generally relates to systems for making hydrophobic epoxy resin compositions including a one part system having at least one ortho-substituted glycidyl ether, at least one ortho, ortho'-disubstituted glycidyl ether, at least one ortho, meta'-disubstituted glycidyl ether, at least one curing agent including at least one ortho-substituted dianilines and/or at least one ortho, ortho'-substituted dianilines, and at least one organic solvent, where they are combined to produce hydrophobic epoxy resin compositions. Embodiments further include at least one toughener and/or at least one filler/pigment.

Yet another aspect of the invention generally relates to methods for forming fiber-reinforced polymer matrix composites including, a one part resin being formulated of at least one ortho-alkyl substituted glycidyl ether, at least one ortho, ortho'-dialkyl substituted glycidyl ether, at least one ortho-, meta'-dialkyl substituted glycidyl ether, at least one unsubstituted glycidyl ether or any combinations thereof, at least one hydrophobic aniline, and at least one organic solvent, where the mixture forms hydrophobic epoxy resin compositions, and where the epoxy resin composition is used to impregnate woven or non-woven fiber cloth, where at least two plies of the resin impregnated cloth and cure under temperature and pressure to form composite laminates. In embodiments, the curing of the composite laminates are accomplished by selecting on of the group consisting of out-of-autoclave, vacuum assisted resin transfer molding, film infusion, and autoclave methods.

Although embodiments of the invention are described in considerable detail, including references to certain versions thereof, other versions are possible. Therefore, the spirit and scope of the appended claims should not be limited to the description of versions included herein.

Prophetic Examples

Prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. An hydrophobic epoxy resin composition, comprising:
   at least one ortho-alkyl substituted bisphenol-type glycidyl ether;
      at least one ortho, ortho'-dialkyl disubstituted bisphenol-type glycidyl ether;
      at least one ortho, meta'-dialkyl disubstituted bisphenol-type glycidyl ether;
      at least one curing agent including at least one ortho-alkyl-substituted dianiline and/or at least one ortho, ortho'-dialkyl-substituted

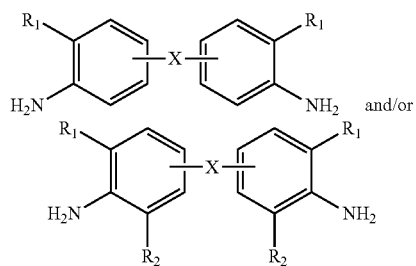

wherein $R_1$ and $R_2$ are $C_1$-$C_{10}$ alkyl and X is alkylene, branched alkylene, CO, O, S, or $SO_2$, at least one organic solvent;

wherein said alkyl and dialkyl substituents are selected to render the composition hydrophobic.

2. The composition according to claim 1, further comprising at least one toughener and/or at least one filler/pigment.

3. The composition according to claim 2, wherein said tougheners for cured epoxies are selected from the group consisting of thermoplastics, elastomers, reactive elastomers in the range of 1% by weight to about 20% by weight.

4. The composition according to claim 2, wherein said fillers or pigments are selected from the group consisting of inorganic and organic compounds in the range of 1% by weight to about 20% by weight.

5. The composition according to claim 1, wherein said at least one ortho-alkyl substituted bisphenol-type glycidyl ether having the formula:

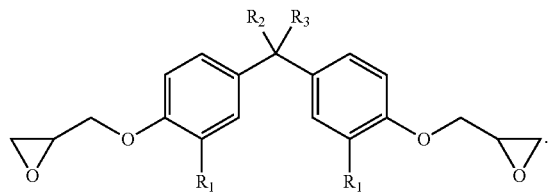

wherein said $R_1$, $R_2$, and $R_3$ are $C_1$-$C_{10}$.

6. The composition according to claim 1, wherein said at least one ortho, ortho'-dialkyl disubstituted bisphenol-type glycidyl ether having the formula:

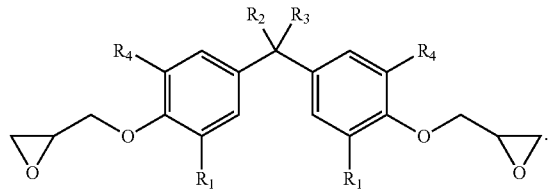

wherein said $R_1$, $R_2$, $R_3$, and $R_4$ are $C_1$-$C_{10}$.

7. The composition according to claim 1, wherein said at least one ortho, meta-dialkyl disubstituted bisphenol-type glycidyl ether having the formula:

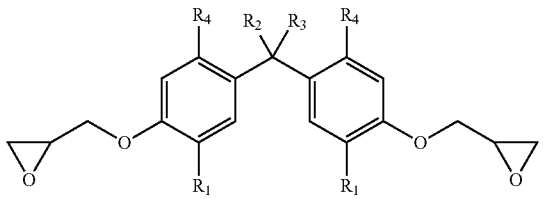

wherein said $R_1$, $R_2$, $R_3$, and $R_4$ are $C_1$-$C_{20}$.

8. The composition according to claim 1, wherein said bisphenol-type glycidyl ethers are comprised of at least two epoxy functional groups with a molecular weight of 1,000 to 6,000 and an epoxy equivalent weight in the range of 100-300.

9. The composition according to claim 1, further comprising additional said curing agents for said glycidyl ethers are selected from the group consisting of at least one polyanilines, aliphatic polyamines, and polyamides with amine hydrogen equivalent weight in the range of about 20-200.

10. The composition according to claim 1, wherein said at least one organic solvent is selected from the group consisting of aromatic hydrocarbons of about $C_6$-$C_{10}$, ketones, phenols, amides, nitriles, and glycols, and any combinations thereof.

11. The composition according to claim 1, wherein said at least one organic solvent is in the range of about 0.5% by weight to 50% by weight.

12. The composition according to claim 1, wherein boiling points of said at least one organic solvent is in the range of about 40-200° C.

13. A system for making hydrophobic epoxy resin compositions, comprising:
a one part system having at least one ortho-alkyl substituted bisphenol-type glycidyl ether;
at least one ortho, ortho'-dialkyl disubstituted bisphenol-type glycidyl ether;
at least one ortho, meta'-dialkyl disubstituted bisphenol-type glycidyl ether;
at least one curing agent including at least one ortho-alkyl substituted dianiline and/or at least one ortho, ortho'-dialkyl substituted dianiline, and
at least one organic solvent,
wherein said alkyl substituted bisphenol-type glycidyl ethers, said at least one curing agent, and said at least one organic solvent are combined to produce hydrophobic epoxy resin compositions.

14. The system according to claim 13, further comprising at least one toughener and/or at least one filler/pigment.

* * * * *